(12) United States Patent
Wright, Jr. et al.

(10) Patent No.: US 7,963,952 B2
(45) Date of Patent: Jun. 21, 2011

(54) EXPANDABLE SHEATH TUBING

(76) Inventors: John A. Wright, Jr., Lexington, MA (US); Todd A. Peavey, Salem, MA (US); Andrea B. Kolber, Tonawanda, NY (US); Lee A. Core, Cambridge, MA (US)

(*) Notice: Subject to any disclaimer, the term of this patent is extended or adjusted under 35 U.S.C. 154(b) by 1309 days.

(21) Appl. No.: 10/921,484

(22) Filed: Aug. 19, 2004

(65) Prior Publication Data
US 2005/0080430 A1 Apr. 14, 2005

Related U.S. Application Data

(60) Provisional application No. 60/496,168, filed on Aug. 19, 2003.

(51) Int. Cl.
*A61M 25/00* (2006.01)
*A61M 5/178* (2006.01)
*A61M 29/00* (2006.01)

(52) U.S. Cl. ............ 604/264; 604/164.01; 604/523; 604/524; 606/198

(58) Field of Classification Search .......... 493/918; 53/469; 604/14, 90, 104, 164.03, 264; D24/112, D24/118
See application file for complete search history.

(56) References Cited

U.S. PATENT DOCUMENTS

| | | |
|---|---|---|
| 3,294,631 A | 12/1966 | Lorenz et al. |
| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,836,204 A | 6/1989 | Landymore et al. |
| 4,840,623 A | 6/1989 | Quackenbush |
| 4,902,508 A | 2/1990 | Badylak et al. |
| 4,909,787 A | 3/1990 | Danforth |
| 4,915,107 A | 4/1990 | Rebuffat et al. |
| 4,917,089 A | 4/1990 | Sideris |

(Continued)

FOREIGN PATENT DOCUMENTS
DE          9413645 U1     10/1994
(Continued)

OTHER PUBLICATIONS

International Search Report, International Application No. PCT/US03/17390, mailed on Oct. 6, 2003, 4 pgs.

(Continued)

*Primary Examiner* — Nicholas D Lucchesi
*Assistant Examiner* — Ian K Holloway (57) ABSTRACT

An expandable catheter accommodates a medical device that is being removed from a body with a larger diameter than the catheter. The same catheter may be used to reposition a device within the body to an alternative delivery site. A catheter or sheath may be used to deliver a medical device, surgical instrument, or biological sample.

26 Claims, 5 Drawing Sheets

U.S. PATENT DOCUMENTS

| | | | |
|---|---|---|---|
| 4,921,479 A | 5/1990 | Grayzel | |
| 4,956,178 A | 9/1990 | Badylak et al. | |
| 5,021,059 A | 6/1991 | Kensey et al. | |
| 5,037,433 A | 8/1991 | Wilk et al. | |
| 5,041,129 A | 8/1991 | Hayhurst et al. | |
| 5,049,131 A | 9/1991 | Deuss | |
| 5,078,736 A | 1/1992 | Behl | |
| 5,106,913 A | 4/1992 | Yamaguchi et al. | |
| 5,108,420 A | 4/1992 | Marks | |
| 5,149,327 A | 9/1992 | Oshiyama | |
| 5,163,131 A | 11/1992 | Row et al. | |
| 5,167,363 A | 12/1992 | Adkinson et al. | |
| 5,167,637 A | 12/1992 | Okada et al. | |
| 5,171,259 A | 12/1992 | Inoue | |
| 5,176,659 A | 1/1993 | Mancini | |
| 5,192,301 A | 3/1993 | Kamiya et al. | |
| 5,211,654 A | 5/1993 | Kaltenbach | |
| 5,222,974 A | 6/1993 | Kensey et al. | |
| 5,226,879 A | 7/1993 | Ensminger et al. | |
| 5,236,440 A | 8/1993 | Hlavacek | |
| 5,245,023 A | 9/1993 | Peoples et al. | |
| 5,245,080 A | 9/1993 | Aubard et al. | |
| 5,250,430 A | 10/1993 | Peoples et al. | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,417 A * | 5/1994 | Wilk | 606/114 |
| 5,312,435 A | 5/1994 | Nash et al. | |
| 5,316,262 A | 5/1994 | Koebler | |
| 5,318,588 A * | 6/1994 | Horzewski et al. | 606/198 |
| 5,320,611 A | 6/1994 | Bonutti et al. | |
| 5,334,217 A | 8/1994 | Das | |
| 5,350,363 A | 9/1994 | Goode et al. | |
| 5,354,308 A | 10/1994 | Simon et al. | |
| 5,364,356 A | 11/1994 | Hofling | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,453,099 A | 9/1995 | Lee et al. | |
| 5,478,353 A | 12/1995 | Yoon | |
| 5,480,353 A | 1/1996 | Garza, Jr. | |
| 5,480,424 A | 1/1996 | Cox | |
| 5,486,193 A | 1/1996 | Bourne et al. | |
| 5,507,811 A | 4/1996 | Koike et al. | |
| 5,534,432 A | 7/1996 | Peoples et al. | |
| 5,540,712 A | 7/1996 | Kleshinski et al. | |
| 5,562,632 A | 10/1996 | Davila et al. | |
| 5,577,299 A | 11/1996 | Thompson et al. | |
| 5,601,571 A | 2/1997 | Moss | |
| 5,603,703 A | 2/1997 | Elsberry et al. | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,901 A * | 6/1997 | Alba et al. | 604/96.01 |
| 5,634,936 A | 6/1997 | Linden et al. | |
| 5,643,282 A * | 7/1997 | Kieturakis | 606/114 |
| 5,649,950 A | 7/1997 | Bourne et al. | |
| 5,649,959 A | 7/1997 | Hannam et al. | |
| 5,663,063 A | 9/1997 | Peoples et al. | |
| 5,683,411 A | 11/1997 | Kavteladze et al. | |
| 5,690,674 A | 11/1997 | Diaz | |
| 5,693,085 A | 12/1997 | Buirge et al. | |
| 5,702,421 A | 12/1997 | Schneidt | |
| 5,709,707 A | 1/1998 | Lock et al. | |
| 5,713,864 A | 2/1998 | Verkaart | |
| 5,717,259 A | 2/1998 | Schexnayder | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,772,641 A | 6/1998 | Wilson | |
| 5,776,162 A | 7/1998 | Kleshinski | |
| 5,776,183 A | 7/1998 | Kanesaka et al. | |
| 5,797,960 A | 8/1998 | Stevens et al. | |
| 5,800,516 A | 9/1998 | Fine et al. | |
| 5,810,884 A | 9/1998 | Kim | |
| 5,820,594 A * | 10/1998 | Fontirroche et al. | 604/165.01 |
| 5,823,956 A | 10/1998 | Roth et al. | |
| 5,829,447 A | 11/1998 | Stevens et al. | |
| 5,853,420 A | 12/1998 | Chevillon et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,885,258 A | 3/1999 | Besselink et al. | |
| 5,893,856 A | 4/1999 | Jacob et al. | |
| 5,902,287 A | 5/1999 | Martin | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,691 A | 8/1999 | Querns et al. | |
| 5,944,738 A | 8/1999 | Amplatz et al. | |
| 5,955,110 A | 9/1999 | Patel et al. | |
| 5,976,174 A | 11/1999 | Ruiz | |
| 5,980,505 A | 11/1999 | Wilson | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,019,753 A | 2/2000 | Pagan | |
| 6,024,756 A | 2/2000 | Huebsch et al. | |
| 6,027,519 A | 2/2000 | Stanford | |
| 6,030,007 A | 2/2000 | Bassily et al. | |
| 6,056,760 A | 5/2000 | Koike et al. | |
| 6,071,998 A | 6/2000 | Muller et al. | |
| 6,077,291 A | 6/2000 | Das | |
| 6,077,880 A | 6/2000 | Castillo et al. | |
| 6,079,414 A | 6/2000 | Roth | |
| 6,080,182 A | 6/2000 | Shaw et al. | |
| 6,096,347 A | 8/2000 | Geddes et al. | |
| 6,106,913 A | 8/2000 | Scardino et al. | |
| 6,113,609 A | 9/2000 | Adams | |
| 6,117,159 A | 9/2000 | Huebsch et al. | |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,168,588 B1 | 1/2001 | Wilson | |
| 6,171,329 B1 | 1/2001 | Shaw et al. | |
| 6,174,322 B1 | 1/2001 | Schneidt | |
| 6,174,330 B1 | 1/2001 | Stinson | |
| 6,183,443 B1 | 2/2001 | Kratoska et al. | |
| 6,187,039 B1 | 2/2001 | Hiles et al. | |
| 6,190,353 B1 | 2/2001 | Makower et al. | |
| 6,190,357 B1 | 2/2001 | Ferrari et al. | |
| 6,197,016 B1 | 3/2001 | Fourkas et al. | |
| 6,199,262 B1 | 3/2001 | Martin | |
| 6,206,895 B1 | 3/2001 | Levinson | |
| 6,206,907 B1 | 3/2001 | Marino et al. | |
| 6,214,029 B1 | 4/2001 | Thill et al. | |
| 6,217,590 B1 | 4/2001 | Levinson | |
| 6,221,092 B1 | 4/2001 | Koike et al. | |
| 6,227,139 B1 | 5/2001 | Nguyen et al. | |
| 6,228,097 B1 | 5/2001 | Levinson et al. | |
| 6,231,561 B1 | 5/2001 | Frazier et al. | |
| 6,245,080 B1 | 6/2001 | Levinson | |
| 6,245,537 B1 | 6/2001 | Williams et al. | |
| 6,261,309 B1 | 7/2001 | Urbanski | |
| 6,265,333 B1 | 7/2001 | Dzenis et al. | |
| 6,270,515 B1 | 8/2001 | Linden et al. | |
| 6,277,138 B1 | 8/2001 | Levinson et al. | |
| 6,277,139 B1 | 8/2001 | Levinson et al. | |
| 6,287,317 B1 | 9/2001 | Makower et al. | |
| 6,290,674 B1 | 9/2001 | Roue et al. | |

| | | | | | | |
|---|---|---|---|---|---|---|
| 6,299,635 | B1 | 10/2001 | Frantzen | 2001/0049492 A1 | 12/2001 | Frazier et al. |
| 6,306,150 | B1 | 10/2001 | Levinson | 2002/0010481 A1 | 1/2002 | Jayaraman |
| 6,306,424 | B1 | 10/2001 | Vyakarnam et al. | 2002/0019648 A1 | 2/2002 | Akerfeldt et al. |
| 6,312,443 | B1 | 11/2001 | Stone | 2002/0022859 A1 | 2/2002 | Hogendijk |
| 6,312,446 | B1 | 11/2001 | Huebsch et al. | 2002/0022860 A1 | 2/2002 | Borillo et al. |
| 6,315,791 | B1 | 11/2001 | Gingras et al. | 2002/0026208 A1 | 2/2002 | Roe et al. |
| 6,316,262 | B1 | 11/2001 | Huisman et al. | 2002/0029048 A1 | 3/2002 | Miller |
| 6,319,263 | B1 | 11/2001 | Levinson | 2002/0032459 A1 | 3/2002 | Horzewski et al. |
| 6,322,548 | B1 | 11/2001 | Payne et al. | 2002/0032462 A1 | 3/2002 | Houser et al. |
| 6,328,727 | B1 | 12/2001 | Frazier et al. | 2002/0034259 A1 | 3/2002 | Tada |
| 6,334,872 | B1 | 1/2002 | Termin et al. | 2002/0035374 A1 | 3/2002 | Borillo et al. |
| 6,342,064 | B1 | 1/2002 | Koike et al. | 2002/0043307 A1 | 4/2002 | Ishida et al. |
| 6,344,048 | B1 | 2/2002 | Chin et al. | 2002/0049457 A1 | 4/2002 | Kaplan et al. |
| 6,344,049 | B1 | 2/2002 | Levinson et al. | 2002/0052572 A1 | 5/2002 | Franco et al. |
| 6,346,074 | B1 | 2/2002 | Roth | 2002/0058989 A1 | 5/2002 | Chen et al. |
| 6,348,041 | B1 | 2/2002 | Klint | 2002/0077555 A1 | 6/2002 | Schwartz |
| 6,352,552 | B1 | 3/2002 | Levinson et al. | 2002/0095174 A1 | 7/2002 | Tsugita et al. |
| 6,355,052 | B1 | 3/2002 | Neuss et al. | 2002/0096183 A1 | 7/2002 | Stevens et al. |
| 6,356,782 | B1 | 3/2002 | Sirimanne et al. | 2002/0099389 A1 | 7/2002 | Michler et al. |
| 6,358,238 | B1 | 3/2002 | Sherry | 2002/0099390 A1 | 7/2002 | Kaplan et al. |
| 6,364,853 | B1 | 4/2002 | French et al. | 2002/0103492 A1 | 8/2002 | Kaplan et al. |
| 6,371,904 | B1 | 4/2002 | Sirimanne et al. | 2002/0107531 A1 | 8/2002 | Schreck et al. |
| 6,375,625 | B1 | 4/2002 | French et al. | 2002/0111537 A1 | 8/2002 | Taylor et al. |
| 6,375,671 | B1 | 4/2002 | Kobayashi et al. | 2002/0111637 A1 | 8/2002 | Kaplan et al. |
| 6,379,342 | B1 | 4/2002 | Levinson | 2002/0111647 A1 | 8/2002 | Khairkhahan et al. |
| 6,379,368 | B1 | 4/2002 | Corcoran et al. | 2002/0120323 A1 | 8/2002 | Thompson et al. |
| 6,387,104 | B1 | 5/2002 | Pugsley, Jr. et al. | 2002/0128680 A1 | 9/2002 | Pavlovic |
| 6,398,796 | B2 | 6/2002 | Levinson | 2002/0129819 A1 | 9/2002 | Feldman et al. |
| 6,402,772 | B1 | 6/2002 | Amplatz et al. | 2002/0164729 A1 | 11/2002 | Skraly et al. |
| 6,419,669 | B1 | 7/2002 | Frazier et al. | 2002/0169377 A1 | 11/2002 | Khairkhahan et al. |
| 6,426,145 | B1 | 7/2002 | Moroni | 2002/0177870 A1 * | 11/2002 | Sepetka et al. ............... 606/194 |
| 6,436,088 | B2 | 8/2002 | Frazier et al. | 2002/0183786 A1 | 12/2002 | Girton |
| 6,440,152 | B1 | 8/2002 | Gainor et al. | 2002/0183787 A1 | 12/2002 | Wahr et al. |
| 6,450,987 | B1 | 9/2002 | Kramer | 2002/0183823 A1 | 12/2002 | Pappu |
| 6,460,749 | B1 | 10/2002 | Levinson et al. | 2002/0198563 A1 | 12/2002 | Gainor et al. |
| 6,482,224 | B1 | 11/2002 | Michler et al. | 2003/0004533 A1 | 1/2003 | Dieck et al. |
| 6,488,706 | B1 | 12/2002 | Solymar | 2003/0023266 A1 | 1/2003 | Welch et al. |
| 6,494,846 | B1 | 12/2002 | Margolis | 2003/0028213 A1 | 2/2003 | Thill et al. |
| 6,494,888 | B1 | 12/2002 | Laufer et al. | 2003/0045893 A1 | 3/2003 | Ginn |
| 6,508,828 | B1 | 1/2003 | Akerfeldt et al. | 2003/0050665 A1 | 3/2003 | Ginn |
| 6,514,280 | B1 * | 2/2003 | Gilson ........................ 623/1.11 | 2003/0055455 A1 | 3/2003 | Yang et al. |
| 6,514,515 | B1 | 2/2003 | Williams | 2003/0057156 A1 | 3/2003 | Peterson et al. |
| 6,548,569 | B1 | 4/2003 | Williams et al. | 2003/0059640 A1 | 3/2003 | Marton et al. |
| 6,551,303 | B1 | 4/2003 | Van Tassel et al. | 2003/0065379 A1 | 4/2003 | Babbs et al. |
| 6,551,344 | B2 | 4/2003 | Thill | 2003/0100920 A1 | 5/2003 | Akin et al. |
| 6,585,719 | B2 | 7/2003 | Wang | 2003/0120337 A1 | 6/2003 | Van Tassel et al. |
| 6,585,755 | B2 | 7/2003 | Jackson et al. | 2003/0139819 A1 | 7/2003 | Beer et al. |
| 6,596,013 | B2 | 7/2003 | Yang et al. | 2003/0171774 A1 | 9/2003 | Freudenthal et al. |
| 6,599,448 | B1 | 7/2003 | Ehrhard, Jr. et al. | 2003/0191495 A1 | 10/2003 | Ryan et al. |
| 6,610,764 | B1 | 8/2003 | Martin et al. | 2003/0195530 A1 | 10/2003 | Thill |
| 6,623,508 | B2 | 9/2003 | Shaw et al. | 2003/0204203 A1 | 10/2003 | Khairkhahan et al. |
| 6,623,518 | B2 | 9/2003 | Thompson et al. | 2004/0044361 A1 | 3/2004 | Frazier et al. |
| 6,626,936 | B2 | 9/2003 | Stinson | 2004/0073242 A1 | 4/2004 | Chanduszko |
| 6,629,901 | B2 | 10/2003 | Huang | 2004/0176799 A1 | 9/2004 | Chanduszko et al. |
| 6,666,861 | B1 | 12/2003 | Grabek | 2004/0186444 A1 * | 9/2004 | Daly et al. ..................... 604/247 |
| 6,669,722 | B2 | 12/2003 | Chen et al. | 2004/0210301 A1 | 10/2004 | Obermiller |
| 6,689,589 | B2 | 2/2004 | Huisman et al. | 2004/0215223 A1 * | 10/2004 | Shaw et al. ..................... 606/170 |
| 6,712,804 | B2 | 3/2004 | Roue et al. | 2004/0234567 A1 | 11/2004 | Dawson |
| 6,712,836 | B1 | 3/2004 | Berg et al. | 2005/0025809 A1 | 2/2005 | Hasirci et al. |
| 6,726,696 | B1 | 4/2004 | Houser et al. | 2005/0043759 A1 | 2/2005 | Chanduszko |
| 6,749,600 | B1 * | 6/2004 | Levy ............................ 604/527 | 2005/0113868 A1 | 5/2005 | Devellian |
| 6,828,357 | B1 | 12/2004 | Martin et al. | 2005/0267523 A1 | 12/2005 | Devellian et al. |
| 6,838,493 | B2 | 1/2005 | Williams et al. | 2005/0273135 A1 | 12/2005 | Chanduszko et al. |
| 6,867,247 | B2 | 3/2005 | Williams et al. | 2005/0288786 A1 | 12/2005 | Chanduszko |
| 6,867,248 | B1 | 3/2005 | Martin et al. | 2006/0122647 A1 | 6/2006 | Callaghan et al. |
| 6,867,249 | B2 | 3/2005 | Lee et al. | 2006/0265004 A1 | 11/2006 | Callaghan et al. |
| 6,921,410 | B2 | 7/2005 | Porter | 2007/0010851 A1 | 1/2007 | Chanduszko et al. |
| 7,094,243 | B2 * | 8/2006 | Mulholland et al. .......... 606/108 | 2007/0167981 A1 | 7/2007 | Opolski |
| 2001/0010481 | A1 | 8/2001 | Blanc et al. | | | |
| 2001/0014800 | A1 | 8/2001 | Frazier et al. | | FOREIGN PATENT DOCUMENTS | |
| 2001/0025132 | A1 | 9/2001 | Alferness et al. | EP | 0362113 | 4/1990 |
| 2001/0034537 | A1 | 10/2001 | Shaw et al. | EP | 0474887 A1 | 3/1992 |
| 2001/0034567 | A1 | 10/2001 | Allen et al. | EP | 0 631 791 A | 1/1995 |
| 2001/0037129 | A1 | 11/2001 | Thill | EP | 0 839 549 | 5/1998 |
| 2001/0039435 | A1 | 11/2001 | Roue et al. | EP | 0839549 A1 | 5/1998 |
| 2001/0039436 | A1 | 11/2001 | Frazier et al. | EP | 0 861 632 | 9/1998 |
| 2001/0041914 | A1 | 11/2001 | Frazier et al. | EP | 1 013 227 | 6/2000 |
| 2001/0041915 | A1 | 11/2001 | Roue et al. | EP | 1 046 375 | 10/2000 |
| 2001/0044639 | A1 | 11/2001 | Levinson | EP | 1 222 897 | 7/2002 |

| | | |
|---|---|---|
| WO | WO 96/08286 A | 3/1996 |
| WO | WO 96/25179 | 8/1996 |
| WO | WO-96/31157 | 10/1996 |
| WO | WO 96/31157 | 10/1996 |
| WO | WO-98/07375 A1 | 2/1998 |
| WO | WO-98/08462 | 3/1998 |
| WO | WO-98/16174 | 4/1998 |
| WO | WO-98/18864 | 5/1998 |
| WO | WO-98/29026 | 7/1998 |
| WO | WO-98/51812 | 11/1998 |
| WO | WO-99/05977 | 2/1999 |
| WO | WO-99/18862 | 4/1999 |
| WO | WO-99/18864 | 4/1999 |
| WO | WO-99/18870 | 4/1999 |
| WO | WO-99/18871 | 4/1999 |
| WO | WO-99/30640 | 6/1999 |
| WO | WO 00/27292 | 5/2000 |
| WO | WO 00/44428 | 8/2000 |
| WO | WO-01/08600 | 2/2001 |
| WO | WO-01/19256 | 3/2001 |
| WO | WO-01/21247 | 3/2001 |
| WO | WO-01/28432 | 4/2001 |
| WO | WO-01/30268 | 5/2001 |
| WO | WO 01/49185 | 7/2001 |
| WO | WO-01/78596 | 10/2001 |
| WO | WO-01/93783 | 12/2001 |
| WO | WO-02/17809 | 3/2002 |
| WO | WO 02/24106 | 3/2002 |
| WO | WO-03/024337 | 3/2003 |
| WO | WO-03/053493 A1 | 7/2003 |
| WO | WO-03/053493 A2 | 7/2003 |
| WO | WO-03/059152 | 7/2003 |
| WO | WO-03/063732 A1 | 8/2003 |
| WO | WO 03/077733 | 9/2003 |
| WO | WO-03/082076 | 10/2003 |
| WO | WO 03/092517 | 11/2003 |
| WO | WO-03/103476 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Kimura, A., et al., "Effects of Neutron Irradiation on the Transformation Behavior in Ti-Ni Alloys," Abstract, Proceedings of the Int'l Conf. on Mariensitic Transformations (1992) pp. 935-940.

Nat'l Aeronautics and Space Administration, "55-Nitinol—The Alloy with a Memory: Its Physical Metallurgy, Properties, and Applications," A Report, pp. 24-25.

Ramanathan, G., et al., "Experimental and Computational Methods for Shape Memory Alloys," 15th ASCE Engineering Mechanics Conf., Jun. 2-5, 2003.

Ruiz et al. "The Puncture Technique: A New Method for Transcatheter Closure of Patent Foramen Ovale," Catheterization and Cardiovascular Interventions 53, Wiley-Liss, Inc., 2001, pp. 369-372.

Shabalovskaya, S., "Surface, corrosion and biocompatibility aspects of Nitinol as an implant material," Bio-Medical materials and Engineering, (2002) vol. 12, pp. 69-109.

SMST-2000, "Proceedings of the International Conference on Shape Memory and Superelastic Technologies," Apr. 30 to May 4, 2000, Asilomar Conference Center.

Stöckel, "Nitinol Medical Devices and Implants," SMST-2000 Conference Proceedings, 2001, pp. 531-541.

Uchil, J. "Shape Memory Alloys—Characterization Techniques," Pramana—Journal of Physics, (2002) vol. 58, Nos. 5 & 6, pp. 1131-1139.

Meier, MD, Bernhard et al., "Contemporary Management of Patent Foramen Ovale," American Heart Association, Inc., Circulation, 2003, vol. 107, pp. 5-9.

Athanasion, T., "Coronary Artery Bypass with the Use of a Magnetic Distal Anastomotic Device: Surgical Technique and Preliminary Experience," The Heart Surgery Forum #2004-1024, 2004, 4 pgs.

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

Klima, U., "Magnetic Vascular Port in Minimally Invasive Direct Coronary Artery Bypass Grafting," Circulation, 2004, II-55-II-60.

Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.

Isotalo, T. et al., "Biocompatibility Testing of a New Bioabsorbable X-Ray Positive SR-PLA 96/4 Urethral Stent", The Journal of Urology, vol. 163, pp. 1764-1767, Nov. 1999.

Parviainen, M. et al., "A New Biodegradable Stent for the Pancreaticojejunal Anastomosis After Pancreaticoduodenal Resection: In Vitro Examination and Pilot Experiences in Humans", Pancreas, vol. 21, No. 1, pp. 14-21, 2000.

Ruddy, A.C. et al., "Rheological, Mechanical and Thermal Behaviour of Radipaque Filled Polymers", Polymer Processing Research Centre, School of Chemical Engineering, Queen's University of Belfast , 5 pages.

Vaajanen, A. et al., "Expansion and Fixation Properties of a New Braided Biodegradable Urethral Stent: An Experimental Study in the Rabbit", The Journal of Urology, vol. 169, pp. 1771-1174, Mar. 2003.

International Search Report, International Application No. PCT/US03/35479, mailed Apr. 14, 2004 (2 pgs).

International Search Report, International Application No. PCT/US97/17927, mailed Feb. 10, 1998 (1 pg).

International Search Report, International Application No. PCT/US04/029978, mailed Jan. 26, 2005 (3 pgs).

International Search Report, International Application No. PCT/US04/026998, mailed Apr. 22, 2005 (5 pgs).

International Search Report, International Application No. PCT/US05/015382, mailed Oct. 6, 2005 (4 pgs).

International Search Report, International Application No. PCT/US03/39253, mailed Apr. 19, 2004 (4 pgs).

International Search Report, International Application No. PCT/US03/17715, mailed Mar. 24, 2004 (2 pgs).

International Search Report, International Application No. PCT/US97/14822, mailed Feb. 20, 1998 (2 pgs).

International Search Report, International Application No. PCT/US03/09051, mailed Sep. 29, 2003 (2 pgs).

International Search Report, International Application No. PCT/US03/01050, mailed Jul. 8, 2003 (1 pg).

International Search Report, International Application No. PCT/US02/40850 mailed Jun. 19, 2003 (4 pgs).

International Search Report, International Application No. PCT/US03/35998 mailed Jun. 16, 2004 (4 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US04/022643, mailed Mar. 31, 2005 (2 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US06/009978, mailed Jul. 13, 2006 (2 pgs).

International Search Report, International Application No. PCT/US2007/065541, mailed Aug. 7, 2007 (3 pgs).

European Examination Report, European Application No. 04781644.2, mailed Aug. 23, 2007 (3 Pages).

European Examination Report, European Application No. 03779297.5, mailed Mar. 15, 2007 (6 Pages).
European Search Report, European Application No. 03729663.9, mailed Feb. 20, 2008 (3 Pages).
International Search Report for International Patent Application No. PCT/AU03/00759, filed Jun. 19, 2003.
International Search Report, International Application No. PCT/US05/34276, mailed Oct. 9, 2007.
International Search Report, International Application No. PCT/US07/065546, mailed Oct. 29, 2007. 4 pages.
International Search Report, International Application No. PCT/US2007/065526, mailed Aug. 8, 2007 (5 pgs).

* cited by examiner

EXPANDABLE SHEATH TUBING

CROSS-REFERENCE TO RELATED APPLICATION

This application claims priority to provisional application Ser. No. 60/496,168, filed Aug. 19, 2003, which is expressly incorporated by reference.

BACKGROUND

The inventions relate to a sheath or catheter that has an expandable distal end.

In many minimally invasive medical procedures, an introducer sheath or catheter may be placed in a vessel to gain access to a site within a body for a diagnostic or therapeutic procedure. Sheaths and catheters are used as conduits to pass surgical instruments, implantable devices, or biological matter, such as clots, tissue samples, or other matter. The inner diameter of the sheath is designed as large as possible for the surgical instrument, implant device, or tissue sample to pass through it. It is generally desirable to minimize the outer diameter of the sheath and maximize the inner diameter of the sheath. A small outer diameter is desired to minimize the size of the hole at the insertion site. A smaller outer diameter also provides less disruption to the circulatory pathway. Since the outer diameter may be minimized and the inner diameter may be maximized, the thickness of the wall of the sheath could lack sufficient column strength for insertion into a blood vessel or other circumstances with longitudinally applied forces.

Medical devices that are implanted may require removal from the body or repositioning within the body. The device that is to be removed may be a temporary implant which has performed the desired diagnostic or therapeutic function. Alternatively, a device may be classified as a permanent implant but may require removal for some other reason. Sometimes devices need to be repositioned in the body. One way of repositioning a device is to pull the device back into a catheter (or push the catheter around the device) so that the device is disposed within the catheter. Then the device is repositioned to a desired delivery location and then deployed. The devices that are removed or repositioned may not collapse into a reduced profile configuration easily or completely.

Because the devices may not collapse completely or in a suitable orientation it may be difficult to reconstrain the device in a catheter. Specifically, this difficulty may be compounded by the material that is used to construct the catheter. The catheter walls are optimally designed to be as thin as possible while having sufficient column strength for proper operation. A material commonly selected for the construction of catheters typically has high stiffness or rigidity. The same material properties that are desirable in the construction of the catheter may make the withdrawal of an implant or tissue more difficult because a catheter constructed of a stiff material will not expand to accommodate a device that is being reconstrained after deployment. This can make it awkward to pass surgical instruments, implantable devices, and tissue samples either in or out of the sheath tip.

SUMMARY

It is desirable to have a catheter that is suitable for reconstraining large or awkwardly shaped surgical instruments and implantable devices after delivery such that they may be repositioned or removed from the body, including medical devices that are being removed from a body with a larger diameter than that of the catheter. The same catheter may be used to reposition a device within the body to an alternative delivery site. A catheter or sheath constructed according to this description may be used to deliver a medical device, surgical instrument, or biological sample. These catheters have a reduced risk of splitting or tearing when a device is positioned within the catheter. As used here, the terms sheath and catheter are used interchangeably.

According to one embodiment, a distal tip of a catheter is constructed to expand radially and thus facilitate the retrieval and repositioning of surgical tools, implantable devices, or biological matter that have a larger diameter than the unexpanded diameter of the catheter. The distal end of the catheter may be formed with either a single layer or multiple layers of material which may be the same or different from the materials comprising the rest of the catheter. In one embodiment, the distal end of the catheter may have one or more straight or curved generally longitudinally-oriented slits. The slits extend through the thickness of one or more layers of the catheter. During delivery of a device, the slits may be closed or open depending on desired delivery characteristics. If the device requires removal or repositioning, the slits in the catheter separate and the catheter diameter expands if necessary as the device is retrieved into the catheter. An elastomeric layer holds the sliced portions of the catheter together and provides an expandable layer so that the catheter remains a single piece. The slits may extend longitudinally from the distal end to a location up to 15 cm along the length of the catheter or more. Alternatively, the slits may begin at a location slightly away from the distal end and continue longitudinally for up to 15 cm along the catheter or more.

In another embodiment, one or more zig-zag slits may be provided longitudinally along a length of the distal end of the catheter and in a direction perpendicular to the radial axis of the catheter, or it can have some angle relative to a perpendicular orientation, or they can have an overall curved shape. The zig-zag configuration of the slits may include straight cuts or separations in the catheter. The zig-zag cuts also may be rounded at the peak and/or the valley of the cut, and/or along the length of the cut. In a preferred form, the size of the zig-zag slits are constructed so that in an expanded configuration (e.g., when a device has been retrieved) the teeth of opposing sides of the zig-zag do not completely separate. Thus the catheter minimizes the likelihood of a longitudinal tear of the elastomeric material, if present. It is desirable that the entire device that has been inserted into the catheter remain in the catheter and not extend through any perforations or tears in the catheter.

The formations described above may be used together and other formations may be used to allow for radial expansion of the catheter as the device is being positioned within the catheter. These formations may or may not require longitudinal contraction. These formations can be present along a portion or the entire length of the sheath tip. Other materials can be added to the sheath tip, such as wires for strength, coatings to change friction characteristics, and coatings of a different durometer, or, the device can be made to have a minimal number of parts and portions.

The catheter can be an introducer through which surgical instruments and implantable devices such as stents, filters, occluders, or other devices are inserted into a living body. The catheter can also be a retriever through which tissue or other biological matter, surgical instruments, and implantable devices are withdrawn from a living body. The cut of the catheter material that forms the slits may be aligned with the radial axis or may be slanted or curved. The cut may be formed from a sharp object, such as a knife, or alternative methods may be used to form the slits.

In another embodiment, the catheter or sheath may have a distal end that is partially or wholly comprised of braided material. In such a device that uses a braided configuration, the longitudinal length shortens as the radius expands. This embodiment has the advantage that individual segments of the catheter are not separated as the catheter expands radially.

A radially expandable distal end of a catheter allows surgical instruments, biological matter, and implantable devices, including such devices as may be folded, compressed, or loaded in the sheath in a specialized manner such that the device can be introduced through a smaller diameter delivery sheath than otherwise possible, to be more easily deployed upon delivery to the desired site within the body. A radially expandable distal end of a catheter allows and facilitates retrieval of surgical instruments and implantable devices, including devices that unfold or expand or otherwise deploy in some way after delivery within the body. The expandable distal end can accommodate more easily the volume of a partially or wholly deployed device, and can overcome snags resulting from the geometry of a partially or wholly deployed device, reducing trauma to the vessel through which such instruments or implantable devices must be withdrawn. Once a device is retrieved into the catheter, the sheath tip can further aid in the complete recovery of a device by acting to compress the device. It is desirable that an expandable distal end of a catheter accommodates an article with a larger dimension than that of the catheter.

These and other features and advantages will become apparent from the drawings and detailed description.

BRIEF DESCRIPTION OF THE DRAWINGS

The inventions will be more clearly understood by reference to the following detailed description when considered in conjunction with the accompanying drawings, wherein.

DESCRIPTION OF THE PREFERRED EMBODIMENTS

A catheter can expand radially at its distal end to accommodate an element (e.g., medical device) that is larger than the diameter of the catheter. At times it is desirable, sometimes necessary, to remove or reposition a medical device that has been previously deployed. A catheter as described here allows a device to be removed or repositioned by expanding to accommodate the device as the device is brought within the catheter. According to some embodiments, the catheter is configured to reduce the possibility of tearing the elastomeric layer longitudinally along the catheter by the edges of a surgical instrument or implantable device being removed or repositioned.

Figure 1:
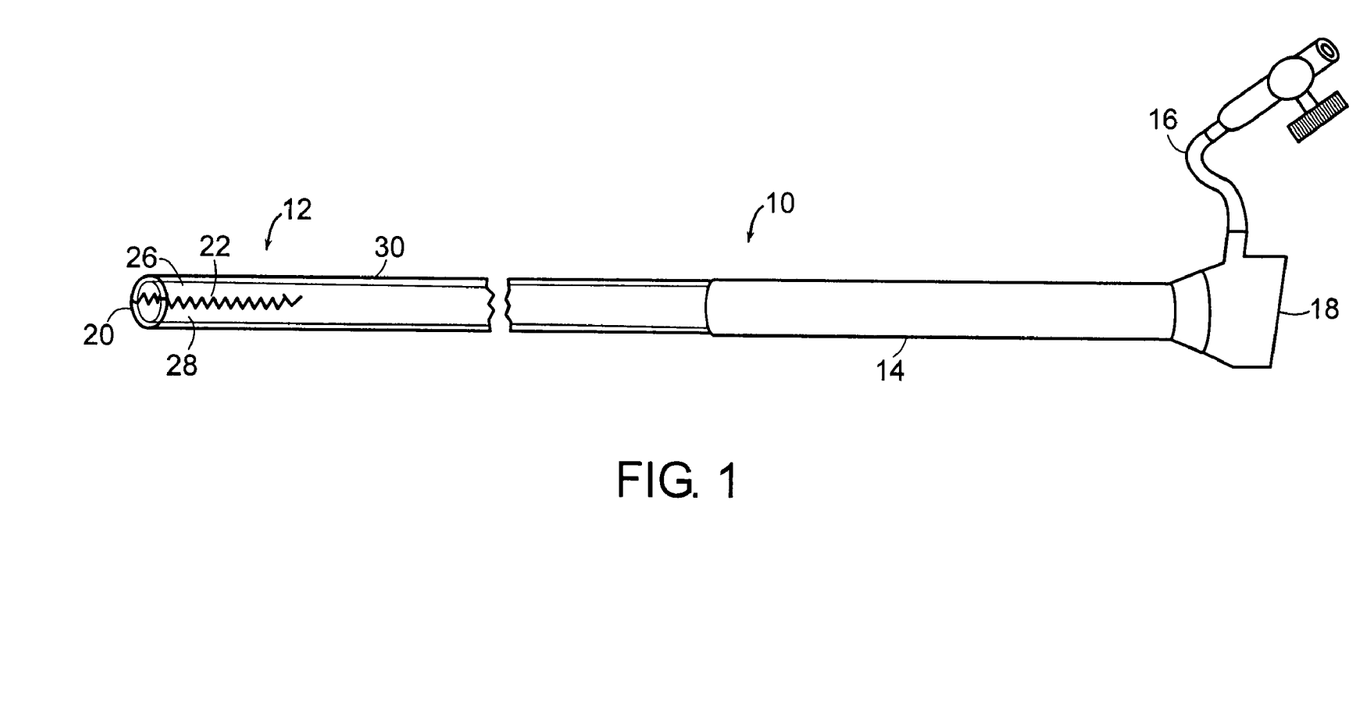
FIG. 1 is an overall view of a catheter constructed according to an embodiment.

Referring to the drawings, wherein like reference numerals designate identical or corresponding parts throughout the several views, and more particularly to FIG. 1 thereof, a catheter 10 is illustrated with a distal end portion 12. The catheter according to this embodiment is adapted to be introduced into the vasculature in a normal procedure as known to those skilled in the art. The expandable distal end portion 12 can expand radially when something having a larger diameter than its normal diameter is introduced into the distal end. The catheter 10 includes a hub portion 14 and side tube 16 which leads into the hub portion 14. A medical instrument or implantable device to be inserted into a patient is placed through a proximal end 18 and is intended to exit the catheter 10 at a distal end 20. When the catheter 10 is used to remove or reposition an implantable device the device enters the catheter at the distal end 20. The implantable device placed, removed or repositioned through the catheter 10 may be a medical device, including, e.g., stents, filters, occluders, or other devices, or a delivery element to deliver a medical device, including stents, filters, occluders, or other devices, into a patient's body.

The catheter 10 can be various lengths, such as between 50 cm and 100 cm. The catheter can be longer or shorter as necessary for a particular application. The diameter of the catheter is typically between 5 and 15 French. Of course, the catheter could have a larger or smaller diameter as a particular application warranted. Typical wall thickness of the catheter 10 can vary greatly depending on the material selected and the length of the catheter.

As illustrated in FIG. 1, the distal end 20 of the catheter 10 is expandable because of zig-zag shaped slit 22 disposed on the distal end of the catheter. A second zig-zag slit (not viewable) is disposed on the other side of the circumference of the catheter. The zig-zag slits create two catheter portions 26 and 28 with a generally semi-circular cross-section along the length of the zig-zag slits. A third zig-zag slit can also be provided to divide the circumference into three sections, and further slits could be provided. In each case, the slits can be centered equally spaced around the circumference, e.g., every 120 degrees for three slits, or they can be spaced at unequal intervals, e.g., at 90 to 180 degrees for three slits. As described in more detail below, when a device is introduced into the distal end of the catheter to be removed or repositioned, the slits allow the catheter portions 26 and 28 to separate to accommodate the device. A clear (as illustrated) elastomeric layer 30 is on the outside of the catheter and enables the catheter to have the required structural integrity.

The elastomeric layer may be disposed on the inside surface of the catheter or on the outside surface of the catheter or both. The layers of the catheter are bonded together, such as through heat bonding, adhesives, or other suitable methods to join the two or more layers. If the elastomeric layer is disposed on the outer surface of the catheter a heat shrink tube may be used. Although the thickness of the layer may vary depending on the needs of a particular application and the material selected, the thickness may be between about 0.001 and 0.025 inches (25 to 625 microns), preferably between about 0.002 and 0.008 inches (50 to 200 microns). Materials for the elastomeric outer cover may include silicone, polyurethane, or polyether-amide block copolymer, such as a material known as Pebax. The elastomeric layer(s) allows the catheter portions 26 and 28 to expand as much as needed to recapture or reposition the device. The elastomeric outer cover can be flush with an inner wall at the distal end of the catheter, or the outer cover can extend beyond the inner wall a short distance to create an overhang that provides a less stiff and "softer" end. This softer tip can help to guide a divide that may have coils or other structures that could get caught if brought back into contact with a stiffer conduit. This overhang would typically have a length of about 0.005 to 0.5 inches (0.125 to 12.5 mm) and preferably about 0.1 inches (2.5 mm), and a thickness of about 0.005 to 0.1 inches (0.125 to 2.5 mm), and preferably about 0.02 to 0.04 inches (0.5 to 1.0 mm). In addition to the end portion, other sections of the catheter can include multiple layers as shown, for example, in application Ser. No. 10/693,398, which is incorporated herein by reference.

Figure 2A:
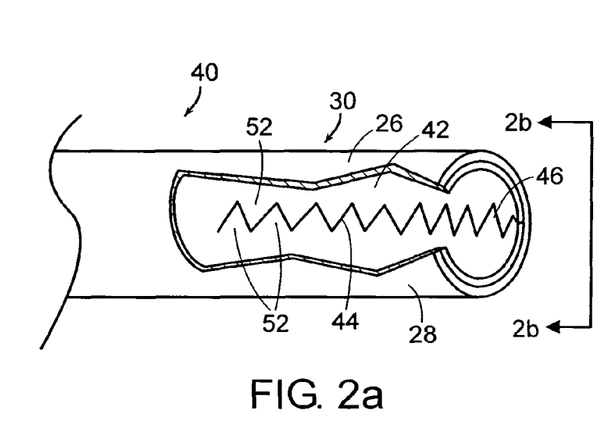
FIG. 2(a) is a side perspective view of a catheter according to an embodiment of the present invention with a portion of an outer elastomeric layer removed.
Figure 2B:
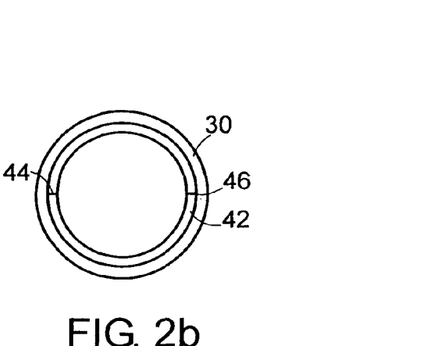
FIG. 2(b) is an end view section taken from lines 2(b)-2(b) in FIG. 2(a)

FIGS. 2(a) and 2(b) illustrate a distal end portion 40 of a catheter. The illustrated embodiment includes a two-wall structure comprised of an elastomeric cover 30 surrounding a relatively high stiffness inner wall 42 (compared to the stiffness of the outer wall). The inner wall has two slits 44, 46 extending in a zig-zag pattern along a longitudinal direction at the distal end of the catheter. The material for the inner wall may include high density polyethylene (HDPE), high-stiffness polyether-amide block copolymer or, high stiffness polyurethane. The zig-zag pattern may extend longitudinally up to 15 cm or more along the length of the distal end portion 40 of the catheter.

The zig-zag pattern forms tooth shapes 52 along the length of the zig-zag pattern. The shapes may be triangular as shown or, alternatively, rectangular, semi-circular or irregular. As depicted in FIG. 2(a), zig-zag slits of the inner wall preferably result in teeth with acute angles and teeth of height equal to one-quarter of the circumference, although the height could vary. Tooth geometry may be variable along the length of the distal end portion 40 of the catheter. For example, larger teeth may be provided at the distal end of the catheter and smaller teeth may be provided towards the proximal end. The geometry of the teeth may change along the length of the slit such that the leading edge of the tooth has an angle to provide a more longitudinal profile. Thus, teeth sizes, widths or shape may change along the length of the tube tip or may change into one of the various slits types discussed below. Of course, more than two longitudinally extending zig-zag slits may be formed at the distal end portion 40 of the catheter. If more than two slits are created, the spacing may be equal along the circumference of a cross-section or, alternatively, the spacing can vary. Varied spacing of the slits may be helpful if a device has an irregular geometry.

Figure 2C:
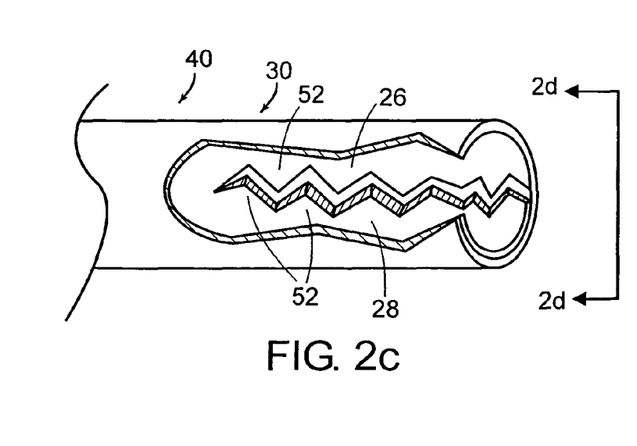
FIG. 2(c) is a side perspective view of a catheter according to an embodiment with a portion of an outer elastomeric layer removed.
Figure 2D:
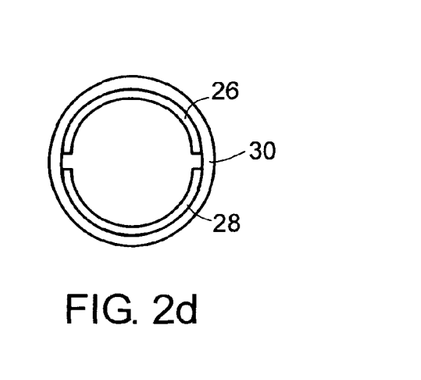
FIG. 2(d) is an end view section taken from lines 2(d)-2(d) in FIG. 2(c)

FIGS. 2(c) and 2(d) illustrate the distal end portion 40 of the catheter in a slightly expanded configuration. The catheter 26, 28 portions with semicircular cross-sections are slightly spread apart and allow for a device with a larger diameter to be inserted into the catheter than would be able to absent the longitudinal slits. The elastomeric layer 30 shown partially removed in FIG. 2(c). FIG. 2(d) illustrates the stretching of the elastomeric layer when the catheter portions 26 and 28 are separated. The slits provide additional flexibility of the inner wall to facilitate expansion, while maintaining longitudinal or column stiffness to inhibit buckling. In the preferred embodiment, the inner and outer layers are bonded in a manner that allows slippage at the teeth edge of the inner layer so that the stress of expansion is distributed to a larger portion of the elastomeric cover.

Figure 2E:
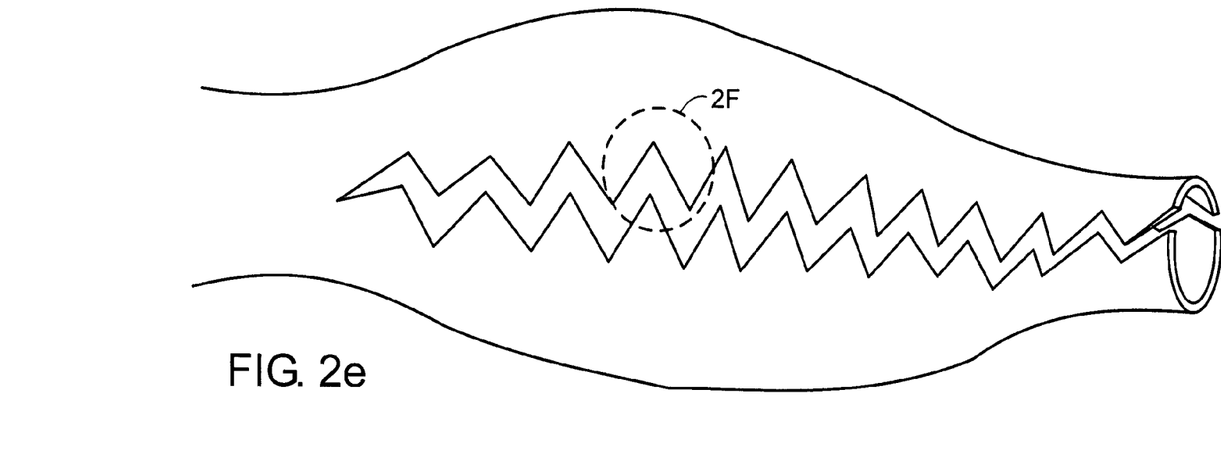
FIG. 2(e) is a detail view of a catheter constructed according to an embodiment illustrating a possible configuration with a device disposed in the distal end of the catheter and a clear elastomeric material used as an outer layer.
Figure 2F:
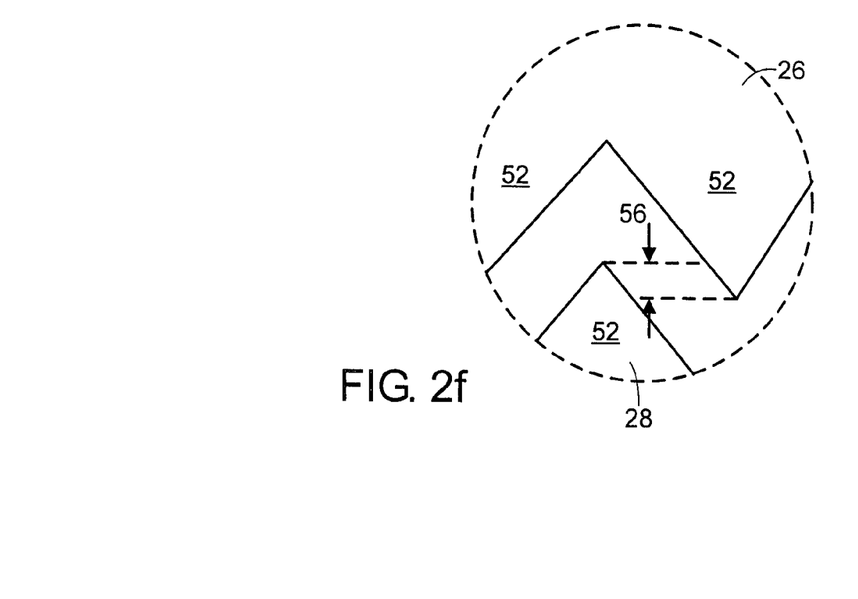
FIG. 2(f) is a detail view of the tooth configuration taken from circle 2(f) in FIG. 2(e)

Referring to FIGS. 2(e) and 2(f), when introducing a device into the catheter after it has been deployed there is a possibility that a portion of the device may have an edge that is sharp enough to tear the elastomeric material as the device is brought into the catheter. The configuration of the teeth that extend in a zig-zag pattern is designed to prevent puncture or tearing of the elastomeric cover. That is, the teeth are designed to be long enough to overlap as much as possible during the introduction of the device. As illustrated in FIG. 2(f), it may be advantageous to extend the elastomeric material beyond the distal end of the stiffer layer. This extension assists in the retrieval of the device by guiding or "funneling" the device into the catheter. The extension may be approximately 0.10 in (0.25 cm). Of course, shorter or longer extensions may be used depending on specific situations. As illustrated in FIG. 2(f), the overlap of the teeth 52 by the distance designated by reference numeral 56 minimizes the possibility that a sharp edge of a device will tear the elastomeric layer as it is drawn into the catheter. Of course, the teeth may be constructed so that they separate sufficiently when a device is introduced into the catheter so that the distance 56 may be reduced to zero. It is also contemplated that the teeth may be designed not to overlap when an object with a much larger diameter is introduced into the catheter. The overlapping ends of the teeth are helpful to make sure that the elastomeric layer is not torn by any sharp edge.

Figure 3A:
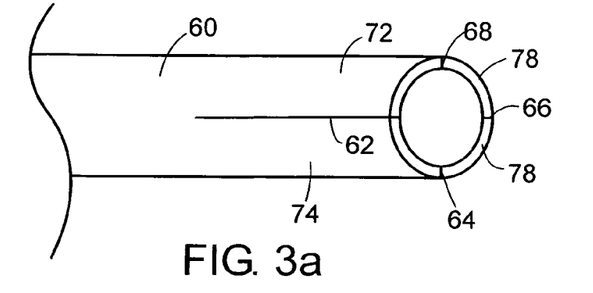
FIGS. 3(a), 3(c), 3(e) and 3(g) are detailed views of alternative embodiments of the distal end of a catheter.
Figure 3B:
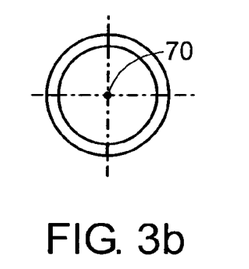
FIGS. 3(b), 3(d), 3(f) and 3(h) are end views of the detail views of FIGS. 3(a), 3(c), 3(e) and 3(g), respectively with the entire outer elastomeric sleeve removed for clarity.
Figure 3C:
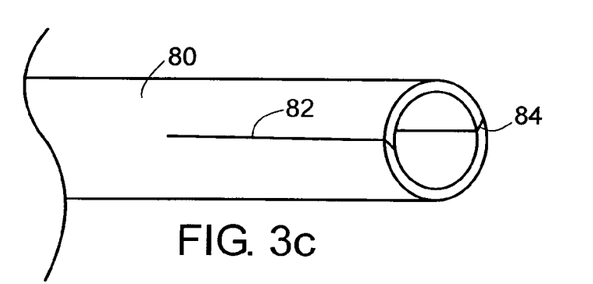
Figure 3D:
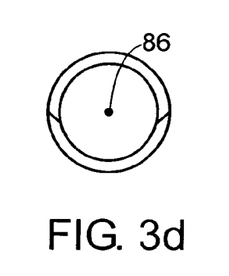
Figure 3E:
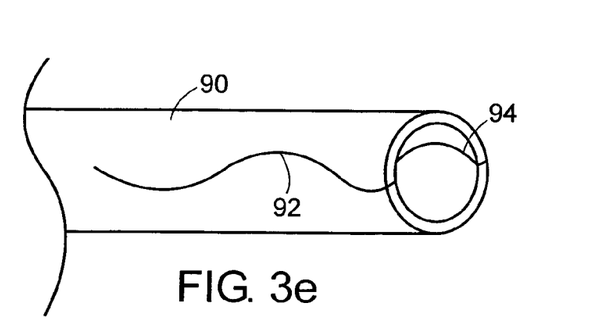
Figure 3F:
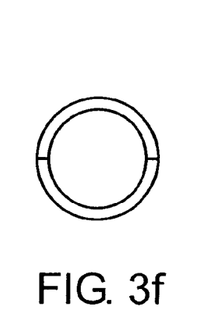
Figure 3G:
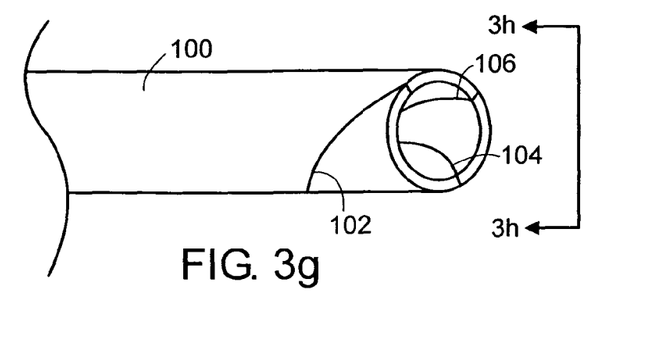
Figure 3H:
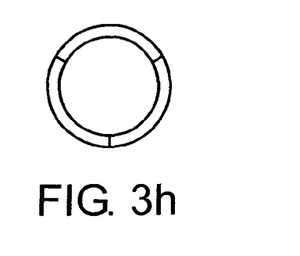

FIGS. 3(a) through 3(h) illustrate other aspects that may be incorporated into catheters described here. For clarity of illustration, the elastomeric layer has not been illustrated, but may or may not be present. Specifically, FIGS. 3(a) and 3(b) show the distal end portion 60 with four slits 62, 64, 66, and 68 disposed longitudinally along a length of the distal end. The length of the slits may be up to 15 cm or more. The slits create catheter quarter sections 72, 74, 76 and 78 which separate and contain a device within the distal end. As illustrated in FIG. 3(b), the slits may extend in a direction radial to the center 70 of the cross-section of the tube. This is a simple, easy to create geometry. FIGS. 3(c) and 3(d) illustrate an alternative geometry for the slit. Specifically, a distal end portion 80 may be provided with two slits 82 and 84 that are oriented at an angle such that they do not intersect the center 86 of a cross section of the catheter end portion 80. Slots of this configuration may assist in keeping the elastomeric layer bonded to the high durometer (inner) layer of the catheter, or, when still overlapped, minimize tearing of the elastomeric layer, if present. FIGS. 3(e) and 3(f) are still other alternative embodiments. As illustrated a distal end portion 90 has two slits 92 and 94 that extend from the distal end of the catheter. The slits 92 and 94 are curved or wavy along the length. The curved slits are relatively easy to construct and may provide advantages over the straight slits by reducing the possibility that sharp edges of a device would tear the elastomeric layer and otherwise facilitating delivery or recovery of an instrument or device. FIGS. 3(g) and 3(h) illustrate still further another embodiment. Here, a distal end portion 100 includes helical slits 102, 104 and 106.

Figure 4A:
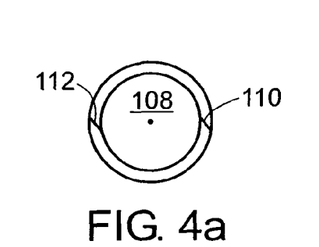
FIGS. 4(a) and 4(b) illustrate slices or cuts at various orientations.
Figure 4B:
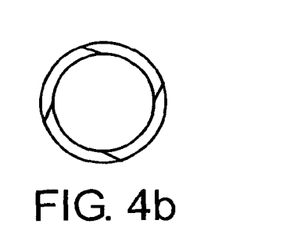

FIGS. 4(a) and 4(b) illustrate the end view of a catheter having alternative configurations for the orientation of the slits that may be used to create any of the slits previously mentioned. FIG. 4(a) has two slits 110 and 112 that are oriented in a manner shown. Similarly, FIG. 4(b) illustrates four slits 120, 122, 124, and 126 that are cut into the catheter in the manner illustrated. Each of these slit configurations can be varied by the number of slits in the catheter and the orientation of the slit. The slit configurations can be applied to each of the embodiments described above.

Figure 5A:
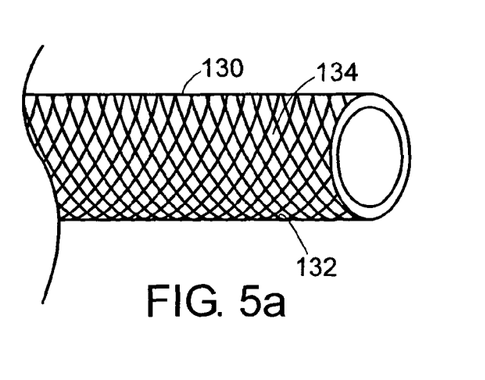
FIGS. 5(a) and 5(b) are detailed views of an alternative embodiment of the distal end of the catheter using a braid.
Figure 5B:
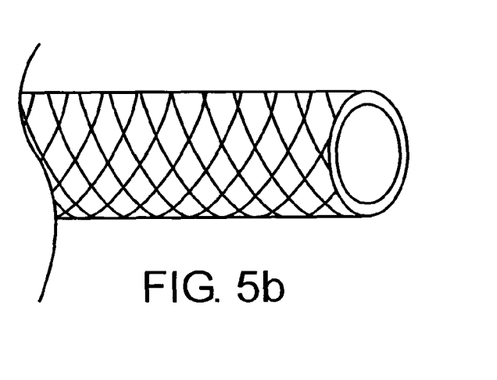

In another embodiment, the expandable catheter end portion 130 includes a wall 132 formed by braided material 134 as illustrated in FIGS. 5(a) and 5(b). The braid 134 has one or more threads of high-stiffness material knitted or woven together. Braid 134 can be obtained commercially from Techflex, Inc. of Sparta, N.J. In this embodiment, the braided distal end may be approximately the same size as or smaller than the rest of the sheath tube. Braided material has the advantage of readily expanding in the radial direction. This advantage is used to accommodate the introduction of a device into the distal end of the catheter. As the catheter radially expands to accommodate a device, the braided material contracts longitudinally, i.e. axially, as depicted in FIG. 5(b). Longitudinal compression of the distal end of the catheter may be achieved by the positive force of the tissue sample, surgical instrument, or implant device being withdrawn into the sheath tip. Alternatively, the longitudinal contraction of the distal end of the catheter may be produced by the positive action of a control rod or contraction cable. The braided expandable distal end of the catheter illustrated in FIGS. 5(a) and 5(b) may or may not include an elastomeric outer cover.

Features of the embodiments described here include the following: the expandable sheath tip facilitates the deployment and retrieval of surgical instruments, implantable devices, and biological matter; use of the expandable sheath tip to partially deploy, expand or inflate an implantable device or surgical instrument before delivery of such implantable device or surgical instrument is specifically envisioned. The sheath tip radially expands to more easily accommodate implantable device or surgical instrument volumes and overcome any device or instrument geometry that may tear an elastomeric sleeve. The sheath tip may or may not be accompanied or enhanced by the addition of other materials such as braids, different tubing, or coatings. The elastomeric material, when present, expands such that the implant will be fully or partially encapsulated within the tip. The elastomeric material, when present, also serves to ensure a controlled and consistent expansion of the tip geometry. In addition to the containment of the retrieved device and protection against cut sheath tip areas, the elastomeric material, when present, may extend past the tip of the sheath to form a highly flexible ring that corrects snags, ensuring the successful entry of the device into the sheath tip.

Once the device is retrieved, the material continues to aid in the complete recovery by compressing the implant to facilitate any remaining size discrepancy between the retrieved device and the dimensions of the full length of the sheath. The expandable sheath tip preserves rigidity, column strength, and stiffness where necessary.

In other configurations of catheters, combinations of the above embodiments are possible. For example, one embodiment includes a high-durometer inner wall with a longitudinally-oriented zig-zag slit, having a cover comprised of a low-durometer braided material. Additionally, the slits may extend the entire length of the catheter so that a device may be pulled through the length of the catheter. Numerous modifications and variations of the present inventions are possible in light of the above teachings. Although the embodiments have been described in detail for the purpose of illustration, it is understood that such detail is solely for that purpose, and variations can be made by those skilled in the art without departing from the spirit and scope of the inventions.

What is claimed is:

1. A catheter sheath for retrieving an object in a body, comprising:
   an expandable distal end, the expandable distal end being a tube including a first layer and a second layer, wherein the first layer is bonded to the second layer, the second layer is positioned outside of the first layer, the first layer comprises a slit that extends from the distal edge of the first layer, a portion of the slit is not parallel to the longitudinal axis of the tube, and the outer surface of the first layer does not contact the inner surface of the first layer, wherein the second layer extends beyond the distal edge of the first layer to create an overhang;
   a proximal end including a port for the passage of objects into the catheter sheath; and
   a tubular percutaneous delivery component located between the proximal and distal ends that creates an uninterrupted conduit between the expandable distal end and the proximal end.

2. The catheter sheath according to claim 1, wherein the slit spirals around the distal end at least one-eighth of a turn.

3. The catheter sheath according to claim 1, wherein the slit is of zig-zag form.

4. The catheter sheath according to claim 1, wherein
   the first layer is an inner layer including at least two slits, in which the at least two slits are generally longitudinally oriented, and a portion of at least one of the at least two slits is not parallel to the longitudinal axis of the tube, and
   the second layer is an outer layer that does not have slits.

5. The catheter sheath according to claim 4, wherein the outer layer is elastomeric.

6. The catheter sheath according to claim 4, wherein the outer layer comprises at least one material selected from the group consisting of silicone, polyurethane, and polyetheramide block copolymer.

7. The catheter sheath according to claim 4, wherein the outer layer is elastomeric and has a thickness in the range of about 0.002 to about 0.008 inches.

8. The catheter sheath according to claim 4, wherein the at least two slits are of a zig-zag cut that forms teeth and the teeth are triangular shaped.

9. The catheter sheath according to claim 4, wherein the at least two slits are of a zig-zag cut that forms teeth and the teeth are semi-circular shaped.

10. The catheter sheath according to claim 4, wherein the outer layer is elastomeric and insures during expansion of the expandable distal end that the teeth remain at least partially interlocked.

11. A catheter sheath for delivery and retrieval of objects during medical procedures, comprising:
    a percutaneous shaft component; and
    an expandable distal end of at least one layer attached to the end of the percutaneous shaft component, including and elastomeric outer cover and a braided layer constructed of braided material that expands axially when a portion of the expandable distal end is contracted longitudinally, wherein the elastomeric outer cover is positioned over the portion of the braided material that receives the object to be retrieved and extends beyond a distal edge of the braided layer to create an overhang.

12. The catheter sheath according to claim 11, wherein the expandable distal end includes a slit layer inside the braided layer, the slit layer including at least two slits, the at least two slits being generally longitudinally oriented.

13. The catheter sheath according to claim 11, further comprising: a control element that controls the diameter of the expandable distal end by adapting the longitudinal contraction of said portion.

14. A method of recovery of an object in a biological vas, comprising:

introducing of a percutaneous catheter sheath, the catheter sheath including a proximal end, an expandable distal end, and a tubular percutaneous component, the proximal end including a port for the passage of objects in the catheter sheath, the tubular percutaneous component located between the proximal and distal ends that creates an uninterrupted conduit between the expandable distal end and the proximal end, and the expandable distal end being a tube including a first layer and a second layer wherein the first layer is bonded to the second layer, the second layer is positioned outside of the first layer, the first layer comprises a slit that extends from the distal edge of the first layer, a portion of the slit is not parallel to the longitudinal axis of the tube, and the outer surface of the first layer does not contact the inner surface of the first layer, wherein the second layer extends beyond the distal edge of the first layer to create an overhang; and recovering the object in the biological vas at least partially into the expandable distal end while causing the expandable distal end to partially expand.

15. The method of recovery according to claim 14, further comprising: redeploying the object in the biological vas after recovering the object at least partially into the expandable distal end.

16. The method of recovery according to claim 14, wherein the first layer is an inner layer including at least two slits, in which the at least two slits are generally longitudinally oriented and a portion of at least one of the at least two slits is not parallel to the longitudinal axis of the tube, and the second layer is an outer layer that is an elastomeric material that does not have slits, the method further comprising: ensuring that the teeth remain at least partially interlocked during expansion of the expandable distal end during manipulation of the object in the biological vas.

17. The method of recovery according to claim 16, further comprising: redeploying the object in the biological vas after recovering the object at least partially into the expandable distal end.

18. The catheter sheath according to claim 1, wherein the distal end has at least a first inner layer and a second outer layer, the second layer is made of a material that is less stiff than the material used to make the first layer, the second layer extending past the first layer at the distal end.

19. The catheter sheath according to claim 17, wherein the second layer extends past the first layer by a distance of 0.005 to 0.5 inches.

20. The catheter sheath according to claim 4, wherein the outer layer is elastomeric, wherein the at least two slits are of a zig-zag cut that forms teeth, and wherein the teeth separate and do not remain at least partially interlocked.

21. A catheter sheath for retrieving an object in a body, comprising:

an expandable distal end, the expandable distal end being a tube including a first layer and a second layer, wherein the first layer is bonded to the second layer, the second layer is positioned outside of the first layer, and the first layer comprises at least two slits that extend from the distal edge of the first layer, wherein the second layer extends beyond the distal edge of the first layer to create an overhang;

a proximal end including a port for the passage of objects into the catheter sheath; and a tubular percutaneous delivery component located between the proximal and distal ends that creates an uninterrupted conduit between the expandable distal end and the proximal end.

22. The catheter sheath according to claim 21, wherein the at least two slits spiral around the distal end at least one-eighth of a turn.

23. The catheter sheath according to claim 21, wherein the at least two slits are generally longitudinally oriented and a portion of at least one of the at least two slits is not parallel to the longitudinal axis of the tube, and the second layer is an outer layer that does not have slits.

24. The catheter sheath according to claim 23, wherein the outer layer is elastomeric.

25. The catheter sheath according to claim 23, wherein the outer layer comprises at least one material selected from the group consisting of silicone, polyurethane, and polyetheramide block copolymer.

26. The catheter sheath according to claim 23, wherein the outer layer is elastomeric and has a thickness in the range of about 0.002 to about 0.008 inches.

* * * * *